United States Patent [19]

Daumas et al.

[11] 4,166,808

[45] Sep. 4, 1979

[54] NOVEL CATALYST FOR OXIDIZING OLEFINS IN α,β-UNSATURATED ALDEHYDES AND PREPARATION THEREOF

[75] Inventors: Jean-Claude Daumas, Orsay; Jean-Yves Derrien, Bourg-la-Reine; Francis Van den Bussche, Ris-Orangis, all of France

[73] Assignee: Rhone-Poulenc Industries, Paris, France

[21] Appl. No.: 832,210

[22] Filed: Sep. 12, 1977

[30] Foreign Application Priority Data

Sep. 14, 1976 [FR] France ............................... 76 27531

[51] Int. Cl.$^2$ .......................... B01J 29/06; B01J 29/16; B01J 23/14
[52] U.S. Cl. ................................ 252/455 R; 252/456; 252/464; 252/470; 260/604 R
[58] Field of Search .................... 252/456, 470, 455 R, 252/464; 260/604 R

[56] References Cited

U.S. PATENT DOCUMENTS

| | | | |
|---|---|---|---|
| 3,804,903 | 4/1974 | Hagiwara | 252/456 X |
| 3,843,555 | 10/1974 | Erpenbach et al. | 252/470 |
| 4,024,074 | 5/1977 | Cairati et al. | 252/470 |
| 4,049,577 | 9/1977 | Childress et al. | 260/604 R |

FOREIGN PATENT DOCUMENTS

1332986 10/1973 United Kingdom ...................... 252/470

*Primary Examiner*—Carl Dees
*Attorney, Agent, or Firm*—Burns, Doane, Swecker & Mathis

[57] ABSTRACT

A novel catalyst composition is disclosed which comprises a catalytically-active metal oxide component containing the oxides of cobalt, molybdenum, bismuth, and iron corresponding to the empirical formula:

$$Co_a Mo_{12} Fe_b Bi_c O_x$$

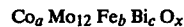

wherein:
a is a value of between about 8 and about 10,
b is a value of between about 0.5 and about 2,
c is a value of between about 0.5 and about 2,
and x equals the sum of 1.5c+1.5b+a+36 and including a crystalline phase having the empirical formula $Bi_2 Mo_2 Fe_2 O_{12}$.

The catalyst composition is prepared by subjecting a conventionally prepared precursor composition to a two-step calcination, comprising two calcining procedures at a temperature of 450°–500° C. and an intermediate cooling to ambient temperature. The novel catalysts exhibit a high activity and selectivity in a process for preparing α,β-unsaturated aldehydes by oxidizing olefins.

25 Claims, No Drawings

NOVEL CATALYST FOR OXIDIZING OLEFINS IN α,β-UNSATURATED ALDEHYDES AND PREPARATION THEREOF

BACKGROUND OF THE INVENTION

1. Field of the Invention

The present invention relates to a novel catalyst for oxidizing olefins into α, β-unsaturated aldehydes in the gaseous phase, to a process for preparing the novel catalyst, and to a process of preparing, α, β-unsaturated aldehydes in the presence of said catalyst. More particularly the invention relates to a novel catalyst comprising oxides of cobalt, molybdenum, bismuth, and iron.

2. Description of the Prior Art

The French Pat. No. 1,604,942 discloses a process for preparing acrolein by oxidizing propylene in the gaseous phase. According to this process a catalytic system is used which comprises a composition of oxides of molybdenum, bismuth, iron, and cobalt wherein the content of the various elements except oxygen is expressed as percentage by atoms as follows: molybdenum: 40-67.6%; bismuth: 1.9-21.7%, iron: 1.6-6.5% and cobalt: 21.0-48.1%. With these catalysts, the structure of which is completely ambiguous, only yields of 70% acrolein at the most can be achieved when 90% of the propylene are converted per single pass. According to the disclosure of the above patent the catalysts are prepared from salts of molybdenum, bismuth, iron and cobalt in the conventional manner by mixing amounts of the salts corresponding to the above cited atomic ratio, adding water or another solvent and heating the reaction mixture in order to cause the different components of the mixture to react with each other. This reaction mixture may then be fixed to a support or mixed with a diluent by milling. Subsequently, the material is calcined at a temperature of 450-550° C. during 5 hours. The calcined material can be used directly or after compressing and milling it in order to increase its mechanical resistancy.

SUMMARY OF THE INVENTION

It is an object of the present invention to provide a catalyst for oxidizing olefins into α,β-unsaturated aldehydes.

It is a further object of the present invention to provide such a catalyst having a high activity in promoting the conversion of the olefin.

It is a further object of the present invention to provide a catalyst which has a high activity in promoting the conversion of the olefin at a relatively low reaction temperature.

It is a further object to provide such a catalyst which exhibits a high selectivity for the formation of an α, β-unsaturated aldehyde, especially a catalyst which selectively favors the formation of acrolein from propylene.

It is a further object of the present invention to provide a process for preparing a catalyst containing a catalytically active metal oxide component, which impairs to this metal oxide component a significantly higher activity than that of an active metal oxide component corresponding to the same empirical formula of a catalyst which is prepared by prior art methods.

In order to accomplish the foregoing objects of the present invention there is provided a catalyst composition comprising a catalytically-active metal oxide component containing the oxides of cobalt, molybdenum, bismuth and iron corresponding to the empirical formula $$Co_a Mo_{12} Fe_b Bi_c O_x$$

wherein:

a is a value of between about 8 and about 10,
b is a value of between about 0.5 and about 2,
c is a value of between about 0.5 and about 2, and
x equals the sum of 1.5c + 1.56b + a + 36, and including a crystalline phase having the empirical formula $Bi_2 Mo_2 Fe_2 O_{12}$.

According to the present invention, there is further provided a process for preparing the above-defined catalyst composition which comprises the steps of:

(a) preparing a liquid reaction mixture comprising water, a cobalt salt, a molybdenum salt, a bismuth salt, and an iron salt, wherein the amount of the salts is equivalent to the ratio of about 8 to about 10 parts per atom of cobalt to about 0.5 to about 2 parts per atom of iron to about 0.5 to about 2 parts per atom of bismuth to about 12 parts per atom of molybdenum, (b) reacting said mixture to form a suspension, (c) eliminating a sufficient amount of water from the suspension to obtain a paste, (d) drying said paste to obtain a solid material, (e) subjecting said solid material to a first calcining step at a temperature of between about 450 and about 500° C. to obtain a calcination product, (f) cooling the calcination product to about ambient temperature, and (g) subjecting the cooled calcination product to a second calcining step at a temperature of between about 450 and about 500° C.

According to the present invention there is also provided a process for preparing α,β-unsaturated aldehydes, e.g., acrolein or methacrolein, by oxidizing olefins, e.g., propylene or isobutylene, in the gaseous phase in the presence of the above-defined catalyst.

Further objects, features and advantages of the present invention will become apparent from the detailed description of the invention and its preferred embodiments which follows.

DETAILED DESCRIPTION OF THE INVENTION

For preparing the catalysts according to the present invention the precursor of the active metal oxide component is prepared in a conventional manner using salts of molybdenum, bismuth, iron, and cobalt as starting materials. Amounts of these salts which are equivalent to the above-cited atomic ratio between the elements are mixed in water or in another solvent and the reaction mixture is heated and agitated in order that the components of the mixture react with each other. Then most of the water is eliminated and the reaction mixture may be adhered to a support or may be dried, ground and mixed with a diluent. Subsequently, the product is calcined twice at a temperature of between about 450 and about 500° C. for about 5 hours. The calcined material can be used directly or after compressing and grinding it for improving the mechanical resistance of the product.

It has been found that depending on the calcining conditions, the catalysts which include oxides of molybdenum, cobalt, iron and bismuth comprise a novel crystallographical phase, which implies to these catalysts properties which are significantly superior to those of the prior art catalysts which correspond to the same empirical formula.

In particular these catalysts permit to obtain very significantly improved yields e.g., in $\alpha,\beta$-unsaturated aldehydes in a process of oxidizing olefins.

Among the catalysts according to the present invention, catalysts of the empirical formula $Co_{10} Mo_{12} Fe_1 Bi_1 O_{49}$ are especially suited.

According to a preferred embodiment of the invention, the active metal oxide component of the catalyst simultaneously comprises the crystalline phase $Bi_2 Mo_2 Fe_2 O_{12}$ and the crystalline phases $Co Mo O_4$ and $Bi_2(MoO_4)_3$.

According to another embodiment of the invention the active metal oxide component of the catalyst simultaneously comprises the crystalline phase $Bi_2 Mo_2 Fe_2 O_{12}$ and the crystalline phases $Co Mo O_4$, $Bi_2(MoO_4)_3$ and $Fe_2(MoO_4)_3$.

Preferably the active component comprises a specific surface of between about 4 and about 10 $m^2/g$ most preferably of about 8 $m^2/g$.

Even though the catalysts according to the present invention can be used in solid massive form, it is advisable, especially in order to favorize a heat exchange, to deposit the catalyst on a support.

Preferably the support is a non-porous support. As nonlimiting examples of support materials there may be cited $SiO_2$, $Al_2O_3$—$SiO_2$, $Al_2O_3$, and diatomaceous earth. The catalyst support may also be made non-porous by enamelling it. Among these support materials alumina is preferred. According to a preferred embodiment of the invention rough alumina balls are used. The roughness can be defined as the ratio between the height of the excrescences and the average diameter of the balls. This ratio preferably is between about 0.1 and about 0.2, but ratios which are outside of this range are not excluded.

The amount of the catalytically active material which is deposited on the support may vary between about 15 and about 30% by weight relative to the total weight of the support and the active component. Preferably catalyst including alumina balls which contain between about 22 and about 25%, e.g., about 24% of the active metal oxide component are used. Yet again, amounts which are outside of the above range are not excluded. The average diameter of the balls can be chosen by anyone skilled in the art depending on what the permissible loss of load of the used reactor is.

For preparing the catalyst according to the present invention a mixture of aqueous solutions of the salts of bismuth, cobalt, iron, and molybdenum is reacted to form a reaction slurry. Water is then eliminated until a paste is obtained which is then dried. The resulting solid is calcined in a two-step calcination comprising a first calcination at a temperature of between about 450° and about 500° C. which is followed by cooling to about ambient temperature and a second calcination at a temperature of between about 450° and about 500° C. Both the first and the second calcination preferably are effected at a temperature of between about 475° and about 485° C., most preferably at a temperature of about 480° C.

The calcination time for each of the calcination steps should be at least 5 hours, e.g., between 5 and 7 hours. According to a preferred embodiment, the material is calcined at a temperature of about 480° C. for 6 hours in each calcination step.

According to a further embodiment of the process according to the present invention prior to the first calcinations, a pre-calcination is effected at a temperature of between about 400° and about 460° C.; the pre-calcined solid is ground, mixed with a conventional binding agent, and the resulting mixture is heated and deposited on a support material and the thus coated support is finally dried.

Preferably the solid is ground to a particle size of less than $400\mu$.

Suitable examples of binding agents are glucose, oxalic acid, malic acid, lactic acid, or tartaric acid, which preferably are applied to the precalcined solids in the form of an aqueous solution. Preferably a 10% aqueous solution of glucose is used. The mixture of water, binding agent and ground pre-calcined solid is heated to a temperature of between about 70° and about 90° C., preferably to a temperature of about 80° C.

According to the present invention $\alpha,\beta$-unsaturated aldehydes are prepared by an oxidation process using the above-defined catalyst. The oxidation process according to the present invention is particularly useful for preparing acrolein by oxidizing propylene.

The catalysts according to the present invention are equally useful for other reactions. As an example, there may be cited the synthesis of acrylonitrile from propylene or the synthesis of methacrolein from isobutylene.

Further to establishing the fact that the presence of the phase $Bi_2 Mo_2 Fe_2 O_{12}$ is the main reason for the outstanding activity of the catalysts according to the present invention, the results of test reactions indicate that the best activity is obtained if, further to the $Bi_2 Mo_2 Fe_2 O_{12}$ phase, a phase $Co MoO_4$, a phase $Bi_2(MoO_4)_3$ and optionally a phase $Fe_2(MoO_4)_3$ are simultaneously present.

The formation of these phases, in particular the $Fe_2(MoO_4)_3$ phase is very sensitive to the reaction conditions during the first and the second calcining step, and thus the relative proportion of these phases in the active metal oxide component depends largely from their calcination conditions.

It has been found that extremely active catalyst are obtained according to the process of the present invention due to the unexpected occurrence of the crystallographical phase $Bi_2 Mo_2 Fe_2 O_{12}$. It has further been found that several additional features should be observed in order to provide for a catalyst which can be used at conditions which at an industrial scale, are advantageous over those which are used in connection with prior art catalysts.

Thus, it is desirable to obtain a catallytically-active component having the best possible texture. It has been found that the more the temperature in the double step calcination increases, the more the specific surface decreases. It has also been found that the phase $Bi_2 Mo_2 Fe_2 O_{11}$ occurs if the temperature in the two-step calcination is between about 450° and 520° C. It is apparent that an ideal temperature for the two-step calcination is that which permits the obtaining of the phase $Bi_2 Mo_2 Fe_2 O_{12}$ and at the same time the largest possible specific surface. It has thus been found that the most advantageous temperature range is between about 475° and 485° C.

On the other hand, it has been found that for preparing a catalyst composition wherein the active component is deposited on a support, a pre-calcination is effected at a temperature of above 460° C. the powder which is obtained after such a pre-calcination takes the form of little grains during the coating of the support balls. If the temperature of the pre-calcination is below 460° C., this phenomenon does not occur.

Another important feature with regard to industrial use is the mechanical resistance of the final catalyst. In effect, it is important that the coating of the active metal oxide component on the support neither separates therefrom nor decomposes into powder.

It is also necessary that the support be as inert as possible. Accordingly, a non-porous support material has been chosen in order to limit the possibilities for any interaction between the support surface and the active component. The stability of active component depends mainly on the roughness of the support balls. Thus, when equal amounts of the active component are used upon coating slightly rough balls, a shell of the active component of a more or less continuous thickness is formed, whereas such a continuous shell is difficultly formed on very rough support balls and the layer of the active component which is situated in the cavities will be mechanically protected by the excrescenses of the support.

The invention will now be described by the following examples:

Example 1

Preparation of a catalyst wherein the catalytically-active metal oxide component corresponds to the empirical formula $Co_{10} Mo_{12} Fe_1 Bi_1 O_{49}$ and is deposited on small enamelled alumina balls.

The precursor of the active metal oxide component was prepared by reacting a solution of ammonium heptamolybdate with a solution of cobalt-, iron-, and bismuth nitrate. Each of the solutions is prepared separately in the following manner:

1938.15 g of cobalt nitrate hydrate having the empirical formula $Co(NO_3)_2.6H_2O$ were dissolved in 450 ml of water at room temperature. The pH value of the resulting solution was 1.8.

268.87 g of iron nitrate hydrate having the empirical formula $Fe(NO_3)_3.6H_2O$ were dissolved in 450 ml of water at room temperature. The pH value of the resulting solution was 0.7.

323.3 g of bismuth nitrate hydrate having the empirical formula $Bi(NO_3)_3.5H_2O$ and 32.5 ml of concentrated nitric acid for promoting the dissolution of the bismuth nitrate were dissolved in 240 ml of water. The pH value of the resulting solution was 0.6.

The three solutions were mixed to form the solution A containing the bismuth, the cobalt and the iron.

The heptamolybdate solution (=solution B) was obtained by dissolving 1411.2 g of ammonium heptamolybdate in 6.75 l of distilled water at room temperature. The pH value of this solution was 5.6.

In order to prepare the precursor of the active metal oxide phase, the nitrate solution A was slowly added to the heptamolybdate solution B at a rate of 10 ml per minute. During this adding procedure, the mixture has to be strongly agitated. An agitator having helicoidal blades turning at a speed of 1100 turns/minute were used. The use of a counter blade is highly advisable.

After the addition was finished, a salmon-colored suspension was formed which was further agitated at room temperature during 30 minutes. During this period of agitation, the pH value stabilized towards 1.1.

The mixture was heated to 80° C. in order to evaporate the water. After 2 hours, a non-fluid paste was obtained and the heating was stopped. The thus obtained paste was spread into a layer having a thickness of about 2 cm and dried under air at a temperature of 120° C. for 16 hours. A solid material which was the precursor of the active metal oxide component was obtained. For calcining, the solid material was cut into pieces of about 1 cm length and placed into the calcination furnace in a layer of about 2 to 3 cm thickness. The pre-calcination was effected at 450° C. for 6 hours. The temperature of the furnace should not rise too fast because of the exothermical decomposition at around 230° C. The rate of the temperature rise was in the range of about 250° C./hour.

The solid material which resulted from the pre-calcination was ground to a granular size of less than 400 microns. An aqueous solution of glucose was prepared by dissolving 10 g of glucose in 100 ml of water at room temperature. 95 g of the ground material were added to the glucose solution and the mixture was then heated to 70° C. for about 30 minutes under strong agitation. The previously prepared suspension was introduced into a coating pan containing 250 g of anamelled rough alumina balls having a diameter of 4.8 mm, which was heated to a temperature of 70° C. The pan was rotated at a temperature of about 80° C. until all of the water was completely evaporated. Subsequently, the resulting coated balls were dried at a temperature of 140° C. for 2 hours. Then they were placed into the calcination furnace in layers of about 2–3 cm thickness and calcinated at 480° C. and faint atmosphere for 6 hours. During this first calcining step, the glucose was slowly cooled and then subsequently subjected to a second calcination at 480° C. Thus, the final catalyst contained about 24% by weight of the active metal oxide component.

The data of the X-ray diffraction spectrum of the phase $Bi_2 Mo_2 Fe_2 O_{12}$ which was obtained from the final catalyst, are shown below:

| d (Å) intereticular distance | Relative Intensity |
|---|---|
| 3.17 | very large |
| 3.14 | very strong |
| 2.91 | strong |
| 2.69 | weak |
| 2.63 | strong |
| 1.87 | very, very weak |

EXAMPLE 2

Preparation of a solid massive catalyst having the empirical formula $Co_{10} Mo_{12} Fe_1 Bi_1 O$.

The precursor was obtained as is described in Example 1.

The precursor is subjected directly to the first calcining step at 480° C., followed by slow cooling and then the second calcining at 480° C. Subsequently, the material was formed into pellets.

EXAMPLES 3–8

The Examples 3–8 serve to demonstrate the improved properties of the catalysts according to the present invention and to point out the influence of different calcining methods.

The various catalysts were tested in a process of preparing acrolein from a reaction mixture containing propylene, air, and water or hydrogen in a reactor having a height of 50 cm and a diameter of 2.1 cm, and containing 100 ml$^3$ of the catalyst. In the Examples 3–7, the catalyst was used wherein the active metal oxide component was deposited on a support of rough enamelled alumina balls having a diameter of 4.8 mm. The balls were coated with an active metal oxide component having the empirical formula $Mo_{12} Co_{10} Bi_1 Fe_1 O_{49}$ in an amount of 23.1% by weight relative to the total weight of the active metal oxide component and the support. The specific surface was 8.5 m²/g and the pore volume was 0.6 cm³/g. The precursor of the active metal oxide component was prepared as is described in Example 1. In Example 8, the solid massive catalyst according to Example 2 having the empirical formula $Mo_{12} Co_{10} Bi_1 Fe_1 O_{49}$ was used in the form of pellets having a height of 3 mm and a diameter of 3 mm.

The gases which were recovered from the reactor and exist during the various tests were mixtures containing nitrogen compounds, oxygen, steam, propylene, acrolein, acrylic acid, acetic acid, acetaldehyde and carbon oxides (CO and $CO_2$). The results of the test Examples 3-8 and composition of the exit gases are given in Table I below. In Table I:

$X_G$ represents the degree of conversion (percentage), that is, the ratio $$\frac{\text{number of mols of propylene converted}}{\text{number of mols of propylene fed}} \times 100$$

$S_X$ represents the selectivity in forming the product X (percentage), that is, the ratio $$\frac{\text{number of mols of product } X \text{ formed}}{\text{number of mols of propylene converted}} \times 100$$

$P_X$ represents the yield in product X. It is equal to the product $X_G + S_X$.

The catalyst in the test Example 3 was prepared in a conventional manner, that is, it was subjected to one final calcination at 500° C. for 6 hours.

The catalyst which was used in test Examples 4 and 5 was prepared according to the present invention. The pre-calcination was effected at 450° C. for 6 hours; the first calcining step was effected at 450° C. and the second at 490° C. each for 6 hours.

The catalyst which was used in Examples 6 and 7 was also prepared according to the present invention. The pre-calcination was effected at 450° C. for 6 hours; the first and the second calcination were both effected at 480° C. for 6 hours each.

TABLE I

| Ex. | wt. g/h/l = $C_3$ | FEED GAS $C_3$ | Air | $H_2O$ or $H_2$ | Temperature °C. bath | Maxi. | Bars relat. | δ A | $X_G$ | $S_A$ | $S_{AA}$ | SELECTIVITIES $S_{CO}$ $S_{CO_2}$ | $S_{C_2H_4O}$ | $S_{C_2H_4O_2}$ | AA | AA | Calcining temp. °C. |
|---|---|---|---|---|---|---|---|---|---|---|---|---|---|---|---|---|---|
| 3 | 140 | 7 | 53 | 40 | 379 | 403 | 0.1 | 68.3 | 91.3 | 74.8 | 13.80 | 5.8 | 3.34 | 1.9 | 88.6 | 81 | 6 h 500° C. c. simple |
| 4 | 140 | 7 | 53 | 40 | 365 | 402 | 0.1 | 79.6 | 96.9 | 82 | 9.2 | 4 | 3.1 | 1.2 | 91.4 | 83.6 | 6 h 450° C. + 6 h 490° C. |
| 5 | 140 | 7 | 53 | 40 | 338 | 361 | 0.1 | 80.7 | 91.5 | 88 | 4.2 | 3.2 | 2.60 | 0.9 | 92.5 | 84.6 | c. double |
| 6 | 140 | 7 | 53 | 40 | 342 | 376 | 0.1 | 79.8 | 94.05 | 84.8 | 6.9 | 3.3 | 3.33 | 1.1 | 91.8 | 86.3 | 6 h 480° C. + 6 h 480° C. |
| 7 | 140 | 7 | 53 | 40 | 358 | 395 | 0.1 | 79 | 96.8 | 81.5 | 9.7 | 3.7 | 3.2 | 1.3 | 91.7 | 88.4 | c. double |
| 8 | 140 | 7 | 53 | 40 | 342 | 402 | 0.1 | 71.6 | 95 | 77.5 | 4 | 17.5 | 1 | 0.2 | 81.5 | 77.5 | |

A = acrolein
AA = acrylic acid

From the data in Table I, it is seen that the yields in acrolein are very markedly improved. From 68.3% in test Example 3, they rise to a range of about 80%.

The degree of conversion was also significantly increased as well as the selectivity with regard to acrolein formation.

A comparison between the test Examples 3 and 5 shows that in order to obtain the same degree of conversion (about 91%) the maximum temperature which is needed with the prior art catalyst is much higher (40° C. higher) than that which is needed with a catalyst according to the present invention. This clearly demonstrates that the higher activity of the catalyst according to the present invention.

The results of the test Examples 6 and 7 were even better due to the fact that double step calcination was effected at the temperature which is the most suitable for the occurrence of the phase $Bi_2 Mo_2 Fe_2 O_{12}$ with the best texture.

The results of Example 8, which were obtained with pelleted massive catalysts show that the latter has a very good activity but the yield and selectivity for the formation of acrolein are less good. This is mainly due to the strong combustion (17.5%) which explains the big difference between the bath temperature and the hot point temperature. In case of such a large difference between these temperatures controlling of the reaction gets difficult. In order to accentuate the high combustion effect, it is available to utilize a catalyst wherein a support is coated with the active metal component.

EXAMPLES 9 to 19

The Examples 9 to 19 demonstrate the preparation of acrolein from propylene using either the catalyst according to the present invention which was used in Examples 6 and 7 (Examples 9, 10, 12, 13, 15, 16, 17, and 18), or the prior art catalyst which was used in Example 3 (Examples 11, 14 and 19).

The tests were effected in an industrial reactor having a height of 4 m and a diameter of 25 mm and containing 2 l of the catalyst.

The test results are summarized in Table II below. The results in the Table confirm that the activity of the prior art catalyst is less good as compared with that of the catalyst according to the present invention.

The prior art catalyst was not active enough for use under industrial conditions such as a propylene load of 192 to 215 g/h/l of the catalyst.

TABLE II

| | | FEED GAS | | | Temp. °C. | | Pres- sure | | | | | | SELECTIVITIES | | | | |
|---|---|---|---|---|---|---|---|---|---|---|---|---|---|---|---|---|---|
| | Wt. g/ | | | H₂O or | O₂/ | | | | | | | | | $S_{CO}$ | | | | |
| Ex. | h/l | $C_3$ | Air | $H_2$ | $C_3$ | bath | Maxi. | bars | δA | $X_G$ | $S_A$ | $S_{AA}$ | $CO_2$ | $C_{C_2H_4O}$ | $S_{C_2H_4O_2}$ | $S_{A+AA}$ | δA+AA | |
| 9 | 138 | 7 | 57 | 36 | 2.0 | 359 | 395 | 1.6 | 74.1 | 98.1 | 75.5 | 13.3 | 5.6 | 4.0 | 1.6 | 88.8 | 87.1 | |
| 10 | 138 | 7 | 57 | 36 | 2.0 | 345 | 375 | 1.6 | 78.7 | 96.7 | 81.4 | 9.4 | 4.1 | 4.2 | 1.2 | 90.8 | 87 | |
| 11 | 138 | 6.6 | 53 | 40.4 | 1.8 | 373 | 409 | 1.6 | 73.9 | 95.3 | 78 | 14 | 3.6 | 2.9 | 1.6 | 92 | 87.7 | * |
| 12 | 161 | 7 | 57 | 36 | 2 | 350 | 392 | 1.6 | 74.1 | 95.2 | 77.8 | 12.1 | 6.6 | 3.5 | 0.2 | 89.9 | 85.4 | |
| 13 | 161 | 7 | 57 | 36 | 2 | 320 | 362 | 1.6 | 77.5 | 90 | 86.2 | 5.1 | 4.7 | 3.1 | 0.9 | 91.3 | 83.2 | |
| 14 | 161 | 6.5 | 59.3 | 34.5 | 2 | 370 | 408 | 1.6 | 69 | 93 | 74.5 | 15 | 5.6 | 4.2 | 0.8 | 89.4 | 83.2 | * |
| 15 | 192 | 7 | 57 | 36 | 2 | 359 | 395 | 1.6 | 77.6 | 95.5 | 81.2 | 10.9 | 3.2 | 4.1 | 1.2 | 92.2 | 88.1 | |
| 16 | 192 | 7 | 57 | 36 | 2 | 348 | 381 | 1.6 | 78.2 | 92.5 | 84.5 | 7.8 | 3.1 | 3.7 | 1.2 | 92.4 | 85.4 | |
| 17 | 215 | 7 | 57 | 36 | 2 | 372 | 410 | 1.6 | 76.2 | 95.3 | 79 | 13.3 | 3.5 | 3.3 | 1.2 | 92.3 | 88 | |
| 18 | 215 | 7 | 57 | 36 | 2 | 361 | 396 | 1.6 | 77.3 | 94.2 | 82 | 10 | 3.6 | 3.7 | 1.2 | 92.0 | 86.7 | |
| 19 | 192 | 7 | 57 | 36 | 2 | 370 | 407 | 1.6 | 69 | 88 | 78.4 | 13 | 3.6 | 3.5 | 1.5 | 91.4 | 80.4 | * |

* = prior art catalyst

While the invention has now been described with reference to certain preferred embodiments, and exemplified with respect thereto, the skilled artisan will appreciate that various changes, modifications, substitutions, and omissions, may be made without departing from the spirit thereof. Accordingly, it is intended that the scope of the present invention be limited solely by that of the following claims.

What is claimed is:

1. A catalyst composition comprising a catalytically active metal oxide component containing the oxides of cobalt, molybdenum, bismuth and iron corresponding to the empirical formula

$$Co_a Mo_{12} Fe_b Bi_c O_x$$

wherein
a is a value of between about 8 and about 10;
b is a value of between about 0.5 and about 2;
c is a value of between about 0.5 and about 2; and,
x equals the sum of 1.5c+1.5b+a+36, and including a crystalline phase having the empirical formula $Bi_2 Mo_2 Fe_2 O_{12}$.

2. The catalyst composition as defined in claim 1, wherein the active metal oxide component corresponds to the empirical formula

$$Co_{10} Mo_{12} Fe_1 Bi_1 O_{49}.$$

3. The catalyst composition as defined in claim 1, wherein the catalytically active metal oxide component simultaneously comprises the crystalline phases $Bi_2 Mo_2 Fe_2 O_{12}$, $Co Mo O_4$ and $Bi_2 (MoO_4)_3$.

4. The catalyst composition as defined in claim 1, wherein the catalytically active metal oxide component simultaneously comprises the crystalline phases $Bi_2 Mo_2 Fe_2 O_{12}$, $Co Mo O_4$, $Bi_2 (MoO_4)_3$ and $Fe_2 (MoO_4)_3$.

5. The catalyst composition as defined in claim 1, wherein the catalytically active metal oxide component has a specific surface of between about 4 m²/g and about 10 m²/g.

6. The catalyst composition as defined in claim 5, wherein the specific surface is about 8 m²/g.

7. The catalyst composition as defined in claim 1, wherein the catalytically active component is deposited on a support.

8. The catalyst composition as defined in claim 7, wherein the support comprises a non-porous and rough support material.

9. The catalyst composition as defined in claim 8, wherein said support material is selected from the group consisting of $SiO_2$, $Al_2O_3$—$SiO_2$, $Al_2O_3$ and diatomaceous earth.

10. The catalyst composition as defined in claim 9, wherein the support material comprises alumina.

11. The catalyst composition as defined in claim 10, wherein the alumina is in the form of balls the average diameter of which is between about 4 and about 5 mm.

12. The catalyst composition as defined in claim 7, wherein the amount of the catalytically active component is between about 15 and about 30% of the total catalyst composition.

13. The catalyst composition as defined in claim 12, wherein the amount of the catalytically active component is about 24% of the total catalyst composition.

14. A process for preparing a catalyst composition as defined in claim 1, which comprises the steps of
(a) preparing a liquid reaction mixture comprising water, a cobalt salt, a molybdenum salt, a bismuth salt and an iron salt, wherein the amount of the salts is equivalent to a ratio of about 8 to about 10 parts per atom of cobalt to about 0.5 to about 2 parts per atom of iron to about 0.5 to about 2 parts per atom of bismuth to about 12 parts per atom of molybdenum;
(b) reacting said mixture to form a suspension;
(c) eliminating a sufficient amount of water from the suspension to obtain a paste;
(d) drying said paste to obtain a solid material;
(e) subjecting said solid material to a first calcining step at a temperature of between about 450° and about 500° C. to obtain a calcination product;
(f) cooling the calcination product to about ambient temperature; and,
(g) subjecting the cooled calcination product to a second calcining step at a temperature of between about 450° and about 500° C.

15. The process as defined in claim 14, wherein the first calcining step (e) is effected at a temperature of between about 475° and about 485° C.

16. The process as defined in claim 14, wherein the second calcining step (g) is effected at a temperature of between about 475 and about 485° C.

17. The process as defined in claim 15, wherein both the first and the second calcining steps are effected at a temperature of about 480° C.

18. The process as defined in claim 14, wherein the calcining time in each of the calcining steps (e) and (g) is at least about 5 hours.

19. The process as defined in claim 17, wherein the calcining time in each of the calcining steps is about 6 hours.

20. The process as defined in claim 14, which prior to the first calcination step (e), further comprises the steps of (ea) pre-calcining the solid material at a temperature of between about 400° and about 460° C.;

(eb) grinding the pre-calcined solid material to form a ground solid material;

(ec) preparing a mixture containing the ground material and a binding agent;

(ed) heating the binding agent containing mixture;

(ef) depositing the binding agent containing mixture on a support material to form a coated support; and, (eg) drying the coated support.

21. The process as defined in claim 20, wherein the pre-calcined solid material is ground to a particle size of less than about 400μ.

22. The process as defined in claim 20, wherein the binding agent is a 10% aqueous solution of glucose.

23. A catalyst composition as defined in claim 1, wherein the X-ray diffraction spectrum of the crystalline phase $Bi_2 Mo_2 Fe_2 O_{12}$ has maximum values at an intereticular distance of 3.17 Å and 3.14 Å, intermediate values at an intereticular distance of 2.91 Å and 2.63 Å and minimum values at an intereticular distance of 2.69 Å and 1.87 Å.

24. The catalyst composition as defined in claim 1, which is the reaction product of a process which comprises the steps of (a) preparing a liquid reaction mixture comprising water, a cobalt salt, a molybdenum salt, a bismuth salt and an iron salt, wherein the amount of the salts is equivalent to a ratio of about 8 to about 10 parts per atom of cobalt to about 0.5 to about 2 parts per atom of iron to about 0.5 to about 2 parts per atom of bismuth to about 12 parts per atom of molybdenum;

(b) reacting said mixture to form a suspension;

(c) eliminating a sufficient amount of water from the suspension to obtain a paste;

(d) drying said paste to obtain a solid material;

(e) subjecting said solid material to a first calcining step at a temperature of between about 450° and about 500° C. to obtain a calcination product;

(f) cooling the calcination product to about ambient temperature; and, (g) subjecting the cooled calcination product to a second calcining step at a temperature of between about 450° and about 500° C.

25. A process for preparing a catalyst composition as defined in claim 1 which comprises the steps of subjecting a solid material comprising Co-, Mo-, Bi-, and Fe compounds wherein the amounts of these compounds is equivalent to a ratio of about 8 to about 10 parts per atom of cobalt to about 0.5 to about 2 parts per atom of iron to about 0.5 to about 2 parts per atom of bismuth to about 12 parts per atom of molybdenum to a first calcining step at a temperature of between about 450° and about 500° C. to obtain a calcination product cooling the calcination product to about ambient temperature; and, subjecting the cooled calcination product to a second calcining step at a temperature of between about 450° to about 500° C.

* * * * *